US008070852B2

United States Patent
Nishimura et al.

(10) Patent No.: US 8,070,852 B2
(45) Date of Patent: Dec. 6, 2011

(54) OXYGEN PARTIAL-PRESSURE CONTROL UNIT AND METHOD OF GAS SUPPLY

(75) Inventors: Hiroshi Nishimura, Kusatsu (JP); Toru Nagasawa, Kusatsu (JP); Haruhiko Matsushita, Kusatsu (JP); Ryusuke Iwasaki, Kusatsu (JP)

(73) Assignee: Canon Machinery Inc., Shiga (JP)

( * ) Notice: Subject to any disclaimer, the term of this patent is extended or adjusted under 35 U.S.C. 154(b) by 367 days.

(21) Appl. No.: 12/517,615

(22) PCT Filed: Dec. 5, 2006

(86) PCT No.: PCT/JP2006/324238
§ 371 (c)(1),
(2), (4) Date: Jun. 4, 2009

(87) PCT Pub. No.: WO2008/068844
PCT Pub. Date: Jun. 12, 2008

(65) Prior Publication Data
US 2010/0065440 A1    Mar. 18, 2010

(51) Int. Cl.
*C01B 13/00*    (2006.01)
(52) U.S. Cl. ...... 95/12; 204/157.5; 204/158.2; 204/277; 205/633
(58) Field of Classification Search ............... 95/8, 12; 204/157.4, 157.5, 158.2, 277; 205/763, 633
See application file for complete search history.

(56) References Cited

U.S. PATENT DOCUMENTS
2008/0163608 A1 *   7/2008   Yacoub .................... 60/276

FOREIGN PATENT DOCUMENTS
JP    2002-326887    11/2002
JP    2004-250283    9/2004

OTHER PUBLICATIONS

International Search Report mailed Jan. 23, 2007 for International Application No. PCT/JP2006/324238.
International Preliminary Report on Patentability and Written Opinion of the International Searching Authority mailed Jun. 18, 2009 for International Application No. PCT/JP2006/324238.

* cited by examiner

*Primary Examiner* — Frank Lawrence, Jr.
(74) *Attorney, Agent, or Firm* — Wenderoth, Lind & Ponack, L.L.P.

(57) ABSTRACT

The oxygen partial pressure control unit includes a gas purification section for purifying the gas having the oxygen partial pressure controlled within a range of from 0.2 to $10^{-30}$ atm, and a tank for storing the purified gas produced by the gas purification section. The purified gas stored within the tank is supplied to the another unit. The oxygen partial pressure control unit includes a circulation circuit including the tank and the gas purification section. The gas filled in the tank 20 is caused to circulate along the circulation circuit, and the purified gas produced by the gas purification section is stored in the tank.

13 Claims, 9 Drawing Sheets

OXYGEN PARTIAL-PRESSURE CONTROL UNIT AND METHOD OF GAS SUPPLY

TECHNICAL FIELD

The present invention relates to an oxygen partial pressure control unit and a gas supply method.

BACKGROUND ART

Conventionally, there is known a method in which a single crystal sample or the like is prepared using an atmospheric gas that has an oxygen partial pressure controlled by an oxygen partial pressure control unit provided with an electrochemical oxygen pump containing a solid electrolyte (Patent Document 1).

An oxygen partial pressure control unit illustrated in FIG. 9 includes a mass flow controller (MFC) 3 that controls the flow rate of an inert gas coming through a valve 2 to a set value, an electrochemical oxygen pump 4 capable of controlling the oxygen partial pressure of the inert gas coming through the mass flow controller 3 to a target value, and an oxygen sensor 5 for supply gas, which monitors the oxygen partial pressure of the inert gas, which has been controlled by the oxygen pump 4, and supplies the gas to a subsequent process (unit) such as a sample preparation unit.

This unit further includes an oxygen partial pressure setting section 6 that sets a desired oxygen partial pressure value, an oxygen partial pressure control section 7 that compares a monitor value of the oxygen sensor 5 with the set value of the oxygen partial pressure setting section 6 to control the oxygen partial pressure of the inert gas to be sent from the oxygen pump 4 to a predetermined value, and an oxygen partial pressure display section 8 that displays the monitor value of the oxygen sensor 5. It should be noted that the oxygen partial pressure of the inert gas is normally approximately $10^{-4}$ atm.

As illustrated in FIG. 10, in the electrochemical oxygen pump 4, electrodes 4b and 4c made of platinum are formed on both the inner surface and the outer surface of a solid electrolytic cylindrical body 4a having oxide ion conductivity. The solid electrolytic cylindrical body 4a is, for example, a zirconia-based solid electrolyte, and is heated by a heater (not shown). The inert gas is supplied in the axial direction from one opening of the solid electrolytic cylindrical body 4a to the other opening thereof. The inert gas is, for example, $Ar+O_2$ ($10^{-4}$ atm). The DC voltage of a DC power supply E is applied between the electrodes 4b and 4c disposed on both the inner and outer surfaces thereof. When a positive voltage is applied to the electrode 4c disposed on the outer surface and a negative voltage is applied to the electrode 4b disposed on the inner surface to cause a current I to flow, oxygen molecules ($O_2$) within the inert gas flowing through the solid electrolytic cylindrical body 4a are electrically reduced into ions ($O^{2-}$), and then are released via the solid electrolyte to the outside of the solid electrolytic cylindrical body 4a as oxygen molecules ($O_2$) again. The oxygen molecules released to the outside of the solid electrolytic cylindrical body 4a are discharged along with auxiliary gases such as air. The inert gas $Ar+O_2$ ($10^{-4}$ atm) supplied to the solid electrolytic cylindrical body 4a is converted, with the oxygen molecules reduced in number, into a processed gas (purified gas) that has the oxygen partial pressure controlled to a target value, and then is fed to the subsequent process (unit).

It should be noted that the oxygen pump 4 of FIG. 10 is capable of performing the pump operation also when a DC voltage having the opposite polarity to the above-mentioned case is applied between the electrodes 4b and 4c disposed on both the inner and outer surfaces of the solid electrolytic cylindrical body 4a. Specifically, when a negative voltage is applied to the electrode 4c disposed on the outer surface and a positive voltage is applied to the electrode 4b disposed on the inner surface, oxygen molecules ($O_2$) in gas, such as air, flowing along the outer surface of the solid electrolytic cylindrical body 4a are electrically reduced into ions ($O^{2-}$) via the solid electrolyte, and then released via the solid electrolyte to the inside of the solid electrolytic cylindrical body 4a as oxygen molecules ($O_2$) again. In this case, the oxygen partial pressure of the inert gas flowing inside the solid electrolytic cylindrical body 4a is increased, and the inert gas is fed to the outside.

By supplying a gas that has the oxygen partial pressure controlled by such an oxygen pump, it becomes possible to perform crystal growth, alloying, heat treatment, a semiconductor manufacturing process, and the like, under an inert gas atmosphere having a controlled oxygen partial pressure.

Patent Document 1: JP 2002-326887 A

DISCLOSURE OF THE INVENTION

Problems to be Solved by the Invention

The oxygen pump illustrated in FIG. 10 uses one solid electrolytic cylindrical body in a shape of a circular pipe. Specifically, a gas to be processed is caused to flow in the axial direction within the inner space of this one solid electrolytic cylindrical body, and while the gas is flowing within the solid electrolytic cylindrical body, a pumping action is performed through ion conduction between the inside and outside of the diaphragm of the solid electrolyte. The flow rate of the gas, which can be processed by such a gas pump, is proportional to the area of contact between the gas to be processed and the inner and outer surfaces of the solid electrolytic cylindrical body. Accordingly, if the flow rate of the gas is to be increased, it is necessary to increase the area of contact between the gas to be processed and the outer surface of the solid electrolytic cylindrical body.

For that purpose, lengthening the solid electrolytic cylindrical body or increasing the diameter of the pipe is conceivable. In order to effectively use an oxygen ion conductive solid electrolyte, it is necessary to lower the resistance value of the oxygen pump as much as possible and to enhance the oxygen permeability of the oxygen pump. The resistance value of the oxygen pump is affected by the shape (surface area and thickness) of the solid electrolyte, the electrode film, the lead terminal, and the like. Of those factors, as to the shape of the solid electrolyte, the resistance value becomes smaller as the surface area becomes larger and the solid electrolyte becomes thinner. Specifically, for a cylindrical body, it is desirable that the diameter and length thereof be larger and the thickness thereof be smaller. However, for the ease with which the solid electrolytic cylindrical body is manufactured and the strength of the solid electrolytic cylindrical body to be used in a heated/high-temperature state, there are limitations in terms of the diameter, the length, and the thickness. Further, as the diameter of the pipe becomes larger, the number of ion conduction reactions sharply declines in the gas to be processed, which is flowing in the core portion of the solid electrolytic cylindrical body. As a result, the gas to be processed, which is flowing in the core portion, passes through without having any reactions, which results in declined control accuracy with respect to the oxygen partial pressure and the like. For this reason, as a matter of course, there is a limitation to simply increasing the diameter of the pipe of the solid electrolytic cylindrical body. This means that the above-mentioned method has a limit on increasing the area of contact between the gas to be processed and the solid electrolytic cylindrical body. Thus, the flow rate of the gas, which can be substantially effectively processed by the gas pump, has been limited, and applications for supply of the gas having a controlled oxygen partial pressure have been limited.

In view of the above-mentioned problems, the present invention has been made, and therefore has an object to provide an oxygen partial pressure control unit and a gas supply method, which are capable of supplying, to another unit such as a sample preparation chamber, a gas (purified gas) that has a controlled oxygen partial pressure without causing a shortage thereof, and allow the another unit to efficiently perform an operation (sample preparation operation) that uses the purified gas.

Means for Solving the Problems

According to the present invention, an oxygen partial pressure control unit includes: a gas purification section for purifying a gas having an oxygen partial pressure controlled within a range of from 0.2 to $10^{-30}$ atm; and a tank for storing the purified gas produced by the gas purification section, the oxygen partial pressure control unit supplying the purified gas stored within the tank to another unit, in which the oxygen partial pressure control unit further includes a circulation circuit including the tank and the gas purification section, and a source gas filled in the tank is caused to circulate along the circulation circuit, and the purified gas produced by the gas purification section is stored in the tank.

With the oxygen partial pressure control unit of the present invention, the source gas filled in the tank is caused to circulate along the circulation circuit, and the purified gas produced by the gas purification section can be stored in the tank. Therefore, it is possible to provide stable supply of the purified gas to the another unit.

The circulation circuit includes: a plurality of the tanks; a first switching means for switching between permission and suspension of supply of the purified gas produced by the gas purification section to each of the plurality of the tanks; and a second switching means for switching between the permission and the suspension of the supply of the purified gas of the each of the plurality of the tanks to the another unit. The circulation circuit is configured to: switch the second switching means to permit the supply of the purified gas from at least one of the plurality of the tanks to the another unit; and switch the first switching means to produce the purified gas for the tank that has finished the supply of the purified gas to the another unit, with the supply of the gas from the at least one of the plurality of the tanks permitted.

The purified gas can be stored in the plurality of the tanks, and hence it is possible to improve the capacity for supplying the purified gas to the another unit. In addition, with the switching of the second switching means, it is possible to supply the purified gas from the at least one of the plurality of the tanks to the another unit, and, with the switching of the first switching means, it is possible to supply the purified gas produced by the gas purification section to the tank that has finished the supply of the purified gas to the another unit. Further, at the time of supplying the gas from the at least one of the plurality of the tanks to the another unit, it is possible to produce the purified gas for the tank that has finished the supply of the purified gas. Therefore, it is possible to supply the purified gas continuously to the another unit without causing a shortage thereof.

The circulation circuit includes: a plurality of the gas purification sections; and a third switching means for switching between permission and suspension of supply of the purified gas from each of the plurality of the gas purification sections to the tank. With the switching of the third switching means, the circulation circuit can cause the gas to circulate through a desired gas purification section among the plurality of the gas purification sections.

With the provision of the plurality of the gas purification sections, it is possible to increase the gas purification capacity, enabling stable supply of the purified gas to the another unit. In addition, with the switching of the third switching means, it is possible to cause the gas to circulate through the desired gas purification section among the plurality of the gas purification sections. Therefore, for example, when demand for the purified gas is low, the purified gas can be produced by one gas purification section, and, when the demand for the purified gas is high, the purified gas can be produced by a plurality of the gas purification sections.

The circulation circuit includes: a plurality of the tanks; a plurality of the gas purification sections; a first switching means for switching between permission and suspension of supply of the purified gas produced by the gas purification sections to each of the plurality of the tanks; a second switching means for switching between the permission and the suspension of the supply of the purified gas of the each of the plurality of the tanks to the another unit; and a third switching means for switching between the permission and the suspension of the supply of the purified gas from each of the plurality of the gas purification sections to the plurality of the tanks. The circulation circuit is configured to: switch the second switching means to permit the supply of the purified gas from at least one of the plurality of the tanks to the another unit; switch the first switching means to produce the purified gas for the tank that has finished the supply of the purified gas to the another unit, with the supply of the gas from the at least one of the plurality of the tanks permitted; and switch the third switching means to cause the gas to circulate through a desired gas purification section among the plurality of the gas purification sections.

The purified gas can be stored in the plurality of the tanks, and hence it is possible to improve the capacity for supplying the purified gas to the another unit. With the provision of the plurality of the gas purification sections, it is possible to increase the gas purification capacity, enabling stable supply of the purified gas to the another unit. In addition, it is possible to produce the purified gas for the tank that has finished the supply of the purified gas to the another unit, with the supply of the gas from the tank permitted, enabling continuous supply of the purified gas to the another unit without causing a shortage thereof. Further, the purified gas can be produced by one gas purification section, or can be produced by a plurality of the gas purification sections.

The gas purification section includes: an electrochemical oxygen pump capable of controlling an inert gas to a target oxygen partial pressure; and an oxygen sensor for monitoring the oxygen partial pressure of the inert gas. Further, the oxygen sensor can be disposed upstream and downstream of the oxygen pump.

According to the present invention, a gas supply method of supplying, to another unit, a purified gas having an oxygen partial pressure controlled within a range of from 0.2 to $10^{-30}$ atm includes: supplying, after storing the purified gas in a plurality of tanks, the purified gas from at least one of the plurality of tanks to the another unit; supplying, after finishing the supplying the gas from the at least one of the plurality of tanks, the purified gas from another one of the plurality of tanks to the another unit; and storing the purified gas in the tank that has finished the supplying the gas during the supplying the purified gas.

With the gas supply method of the present invention, after stored in the plurality of tanks, the purified gas can be supplied from the at least one of the plurality of tanks to the another unit. After the supplying the purified gas to the another unit is finished, the purified gas is supplied from the another one of the plurality of tanks to the another unit. Further, for the tank that has run short of the purified gas, the purified gas can be supplied to and stored in that tank during the supplying the purified gas from the another one of the plurality of tanks.

EFFECTS OF THE INVENTION

According to the present invention, it is possible to store in the tank the purified gas produced by the gas purification section, enabling stable supply of the purified gas to the another unit. In addition, the purified gas is produced from the gas circulating within the circulation circuit, and hence it is possible to produce the purified gas in a clean state, enabling the supply of the purified gas of high quality to the another unit. In other words, with a unit in which the purified gas that has been supplied to the another unit and used is returned and sequentially supplied to the gas purification section, it is difficult to maintain the clean state, and there is a fear of deteriorated quality.

The purified gas can be stored in a plurality of the tanks, and hence it is possible to enhance the capacity for supplying the purified gas to the another device. With the provision of a plurality of the gas purification sections, it is possible to increase the gas purification capacity, enabling stable supply of the purified gas to the another unit. Therefore, it is also possible to handle satisfactorily a unit that requires a large amount of the purified gas, making applications for the gas supply free from limitation.

In addition, with the switching of the first switching means and the second switching means, for a tank that has run short of the purified gas, the purified gas can be stored in that tank during the supplying of the gas from the another tank. Therefore, the purified gas can be continuously supplied to the another unit, and the another unit can stably perform processing that uses the purified gas.

With the switching of the third switching means, it is possible to change the number of the gas purification sections through which the gas circulates, enabling the gas purification capacity to be changed. Therefore, by changing the purification capacity in accordance with the amount of the gas to be used by the another unit of a supply target or the like, it is possible to perform an efficient operation.

The gas purification section includes the electrochemical oxygen pump capable of controlling the oxygen partial pressure of the gas to a target value, and the oxygen sensor that monitors the oxygen partial pressure of the gas. Specifically, the gas having the oxygen partial pressure controlled to the target value can be produced by the oxygen pump, and also, the oxygen partial pressure of this purified gas can be checked. As a result, the gas having the oxygen partial pressure controlled to the target value can be stably supplied to the tank. Further, by disposing the oxygen sensors upstream and downstream of the oxygen pump, it becomes easier to regulate the gas purified by the oxygen pump, enabling the purification of the gas having the oxygen partial pressure controlled more accurately.

With the gas supply method of the present invention, for a tank that has run short of the purified gas, the purified gas can be stored in that tank during the supplying of the gas from the another tank. Therefore, the purified gas can be continuously supplied to the another unit, and the another unit can stably perform the processing that uses the purified gas.

DESCRIPTION OF REFERENCE SYMBOLS

Figure 1:
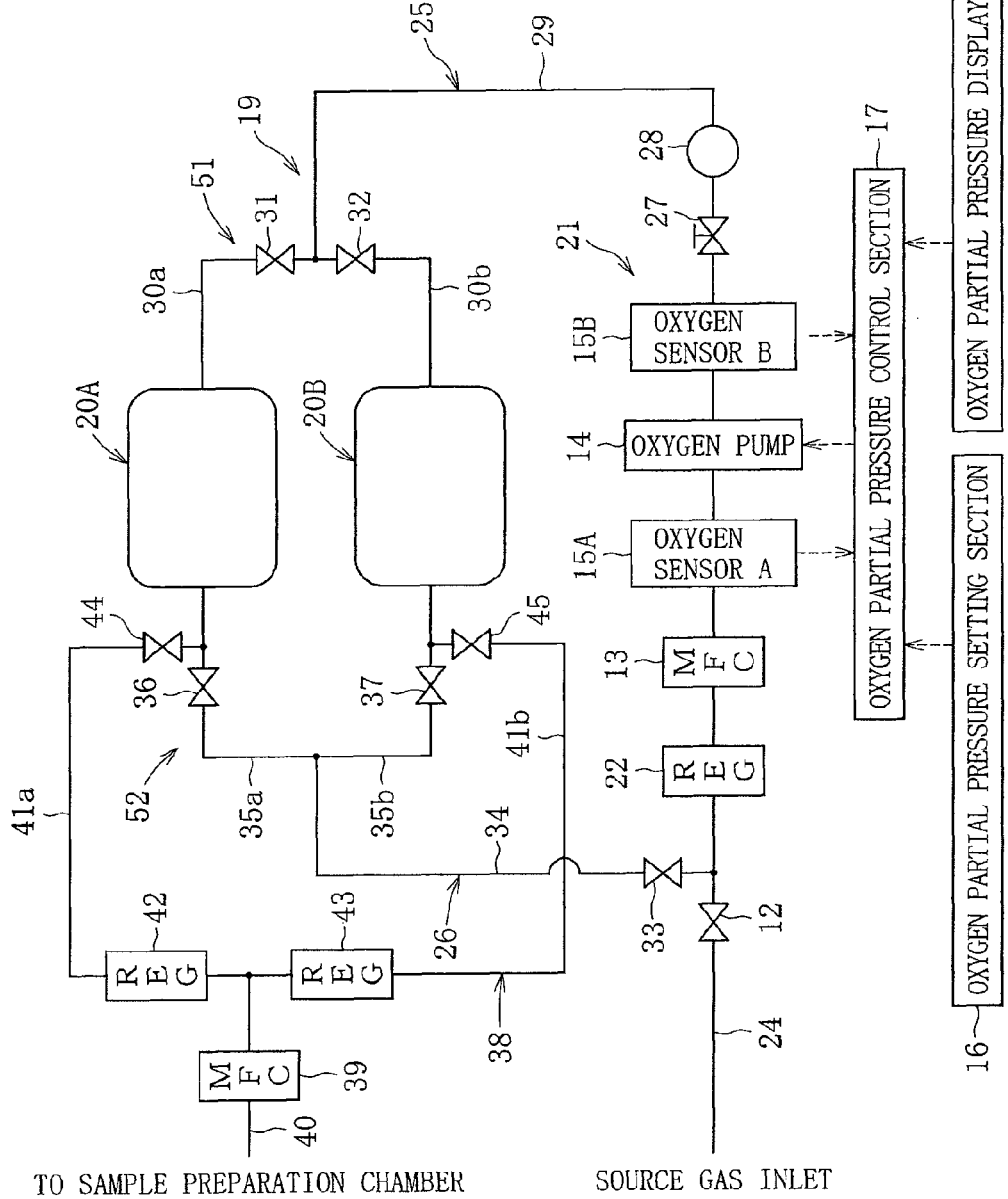
FIG. 1 A simplified schematic view of an oxygen partial pressure control unit representing an embodiment of the present invention.

14 oxygen pump
15A oxygen sensor
15B oxygen sensor
19, 19A, 19B circulation circuit
20, 20A, 20B tank
21, 21A, 21B gas purification section
51 first switching means
52 second switching means
76 third switching means

BEST MODE FOR CARRYING OUT THE INVENTION

FIG. 1 illustrates an oxygen partial pressure control unit according to the present invention. This oxygen partial pressure control unit, which is provided with a circulation circuit 19 including a plurality of (in the example of FIG. 1, two) tanks (buffer tanks) 20A and 20B and a gas purification section 21 that purifies a gas having an oxygen partial pressure controlled within a range of from 0.2 to $10^{-30}$ atm, fills the tanks 20A and 20B with the purified gas produced by the gas purification section 21, and then supplies the purified gas from the tanks 20A and 20B to another unit (for example, sample preparation chamber).

The gas purification section 21 includes an electrochemical oxygen pump 14 capable of controlling the gas to have a target oxygen partial pressure, an upstream oxygen sensor 15A that monitors the oxygen partial pressure of an inert gas before the inert gas flows into the oxygen pump 14, and a downstream oxygen sensor 15B that monitors the oxygen partial pressure of the gas, which is controlled by the oxygen pump 14. Further, upstream of the upstream oxygen sensor 15A, there are disposed a pressure regulating valve (REG) 22 that regulates the pressure of the gas coming through a switching valve 12, and a mass flow controller (MFC) 13 that controls the flow rate of the gas coming through the pressure regulating valve (REG) to a set value.

Figure 10:
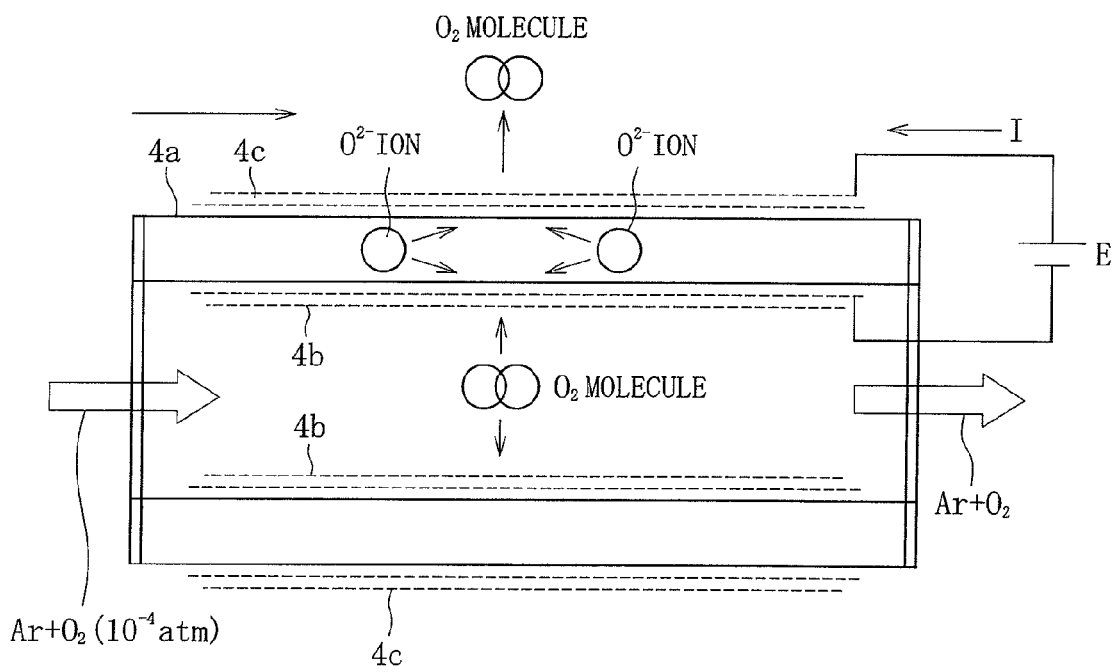
FIG. 10 An explanatory view of a principle of an oxygen pump.

For the oxygen pump 14, a configuration in which electrodes made of platinum are formed on both the inner surface and the outer surface of a solid electrolytic cylindrical body having oxide ion conductivity, that is, a configuration the same as that of an oxygen pump 4 illustrated in FIG. 10, may be employed. Accordingly, a description of the configuration and principle of the oxygen pump 14 is herein omitted.

For the oxygen sensors 15A and 15B, similarly to the above-mentioned oxygen pump 14, the configuration in which electrodes made of platinum are formed on both the inner surface and the outer surface of a solid electrolytic cylindrical body having oxide ion conductivity may be employed. Then, a potential difference between the electrode on the inner surface and the electrode on the outer surface is measured, whereby the oxygen partial pressure can be determined by the Nernst equation of thermodynamics.

Further, this oxygen partial pressure control unit includes: an oxygen partial pressure setting section 16 that sets a desired oxygen partial pressure value; an oxygen partial pressure control section 17, such as a PID control system, which compares monitor values of the upstream oxygen sensor 15A and the downstream oxygen sensor 15B with a set value of the oxygen partial pressure setting section 16, and then controls the oxygen partial pressure of the gas to be sent from the oxygen pump 14 to a predetermined value; and an oxygen partial pressure display section 18 that displays the oxygen partial pressure set value of the above-mentioned oxygen partial pressure setting section 16, and the monitor values of the oxygen sensors 15A and 15B.

An outlet side of the gas purification section 21 is connected to a pair of the tanks 20A and 20B via a first circulation path 25, whereas an inlet side of the gas purification section 21 is connected to the pair of the tanks 20A and 20B via a second circulation path 26.

The first circulation path 25 includes a main body pipe 29 in which a flow rate regulating valve 27 and a pump (for example, diaphragm pump) 28 are interposed, and first and second branch pipes 30a and 30b branching from the main body pipe 29. It should be noted that switching valves 31 and 32 are interposed in the branch pipes 30a and 30b, respectively.

The second circulation path 26 includes a main body pipe 34 in which a switching valve 33 is interposed, and first and second branch pipes 35a and 35b branching from the main body pipe 34. It should be noted that switching valves 36 and 37 are interposed in the branch pipes 35a and 35b, respectively.

The second circulation path 26 is connected to an outflow path 38 for supplying the purified gas into another unit (for example, sample preparation chamber or the like). The outflow path 38 includes a downstream pipe 40 in which an MFC 39 is interposed, a connecting pipe 41a connecting the downstream pipe 40 and the first branch pipe 35a of the second circulation path 26, and a connecting pipe 41b connecting the downstream pipe 40 and the second branch pipe 35b of the second circulation path 26. Pressure regulating valves (REGs) 42 and 43 and switching valves 44 and 45 are interposed in the connecting pipes 41a and 41b, respectively.

Figure 2:
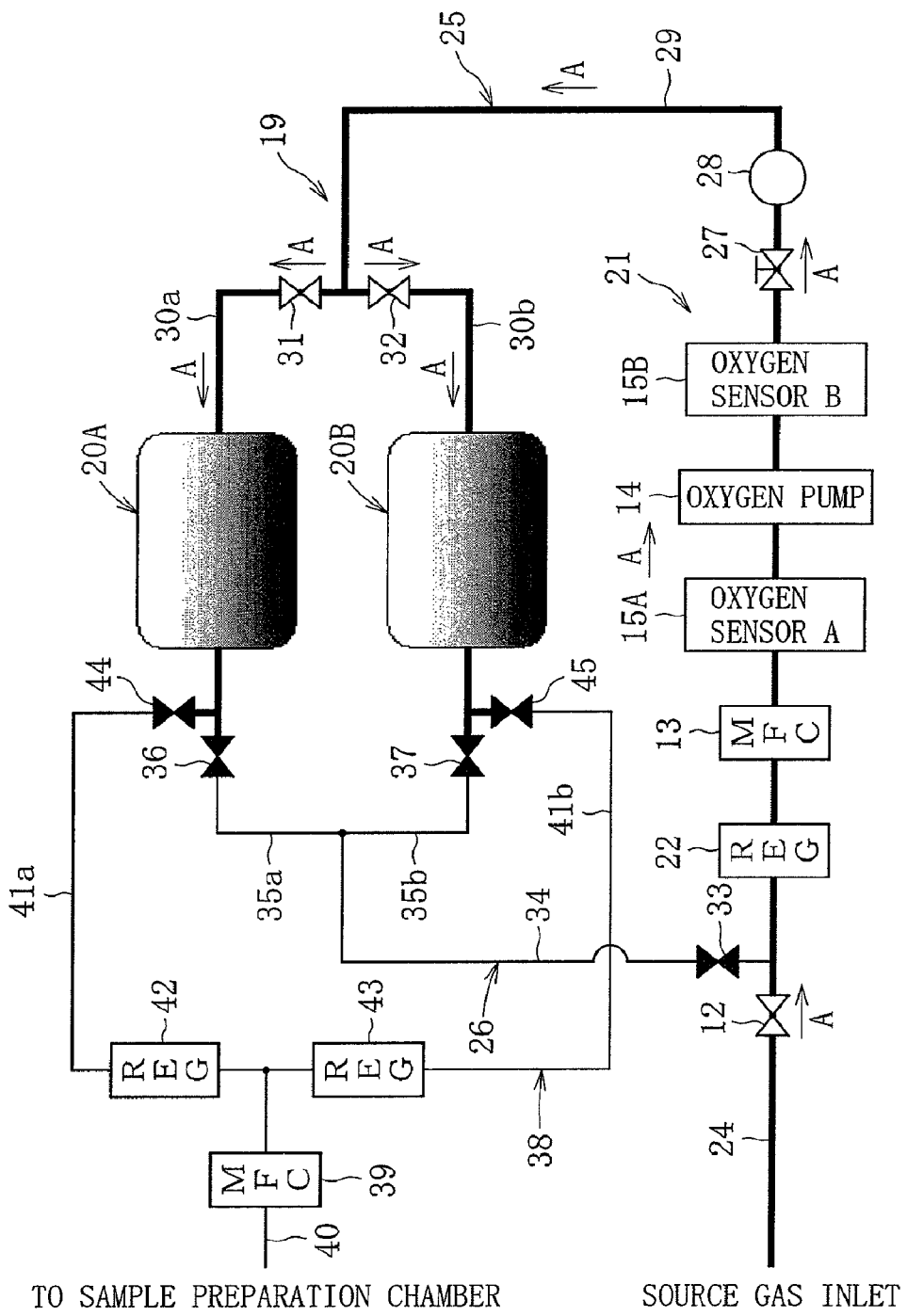
FIG. 2 A simplified schematic view of the oxygen partial pressure control unit representing a process of filling a tank with a source gas.
Figure 3:
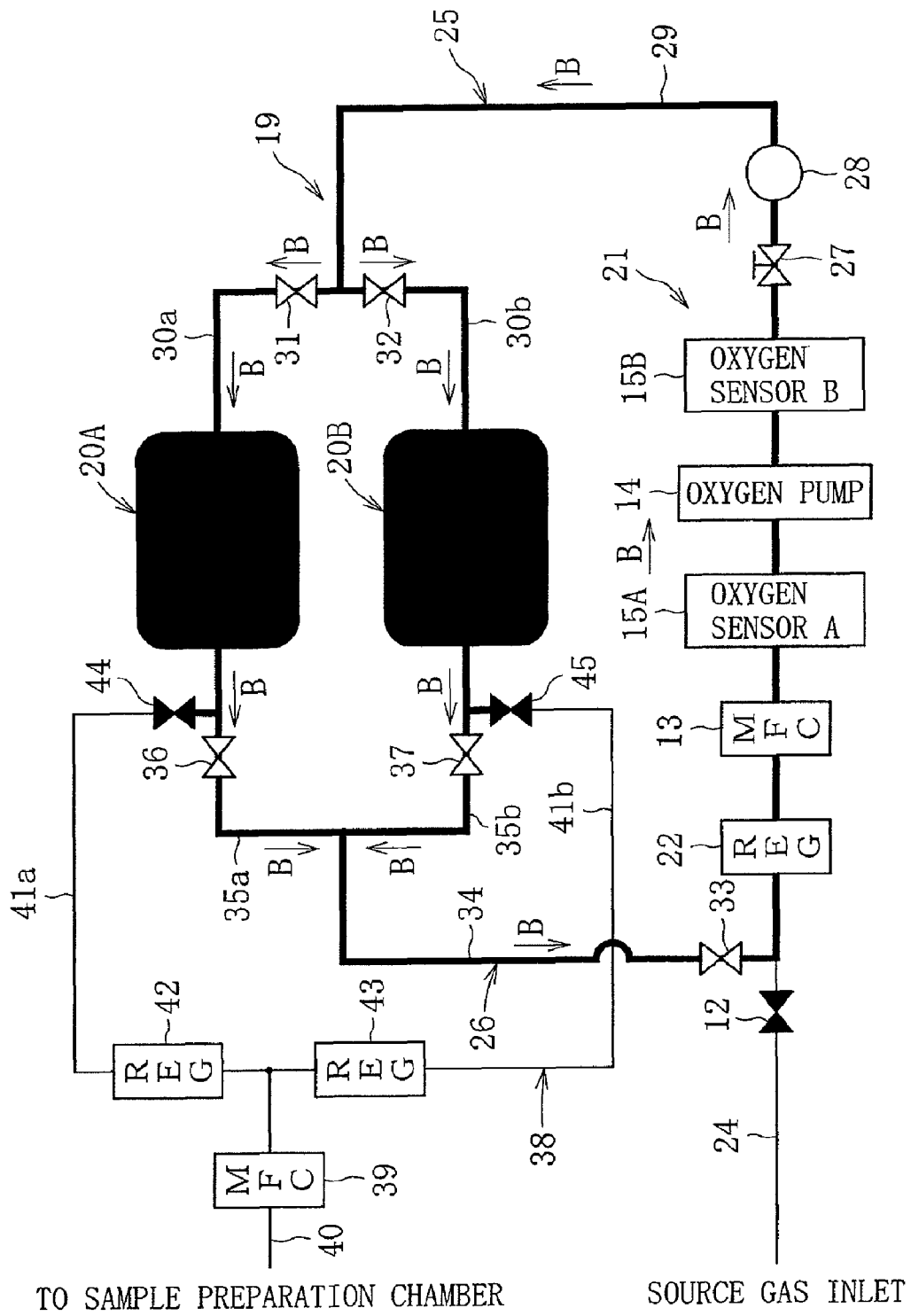
FIG. 3 A simplified schematic view of the oxygen partial pressure control unit representing a process of gas purification.
Figure 4:
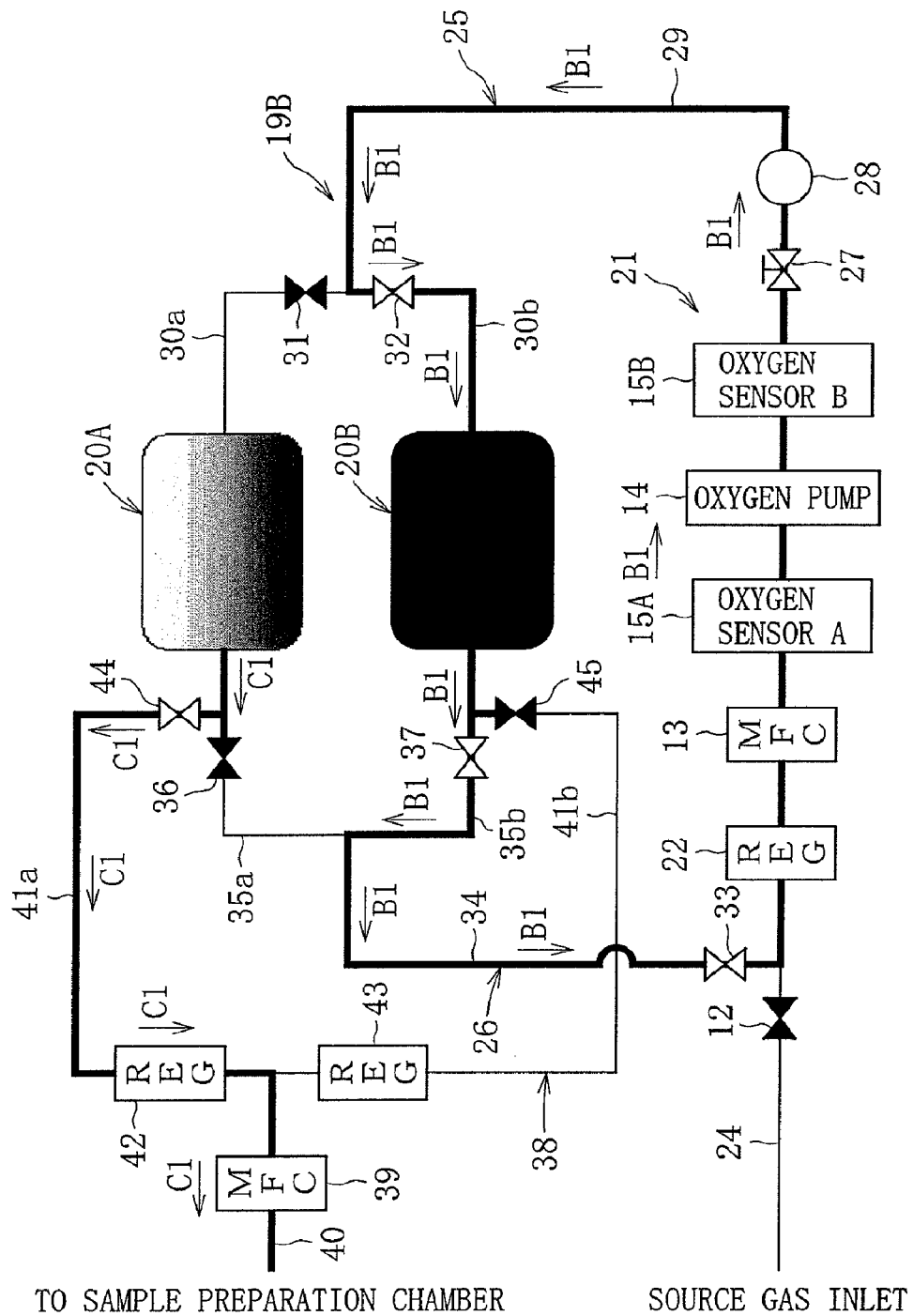
FIG. 4 A simplified schematic view of the oxygen partial pressure control unit representing a process of supplying a purified gas from a first tank to a sample preparation chamber and a purification process of a second tank.
Figure 5:
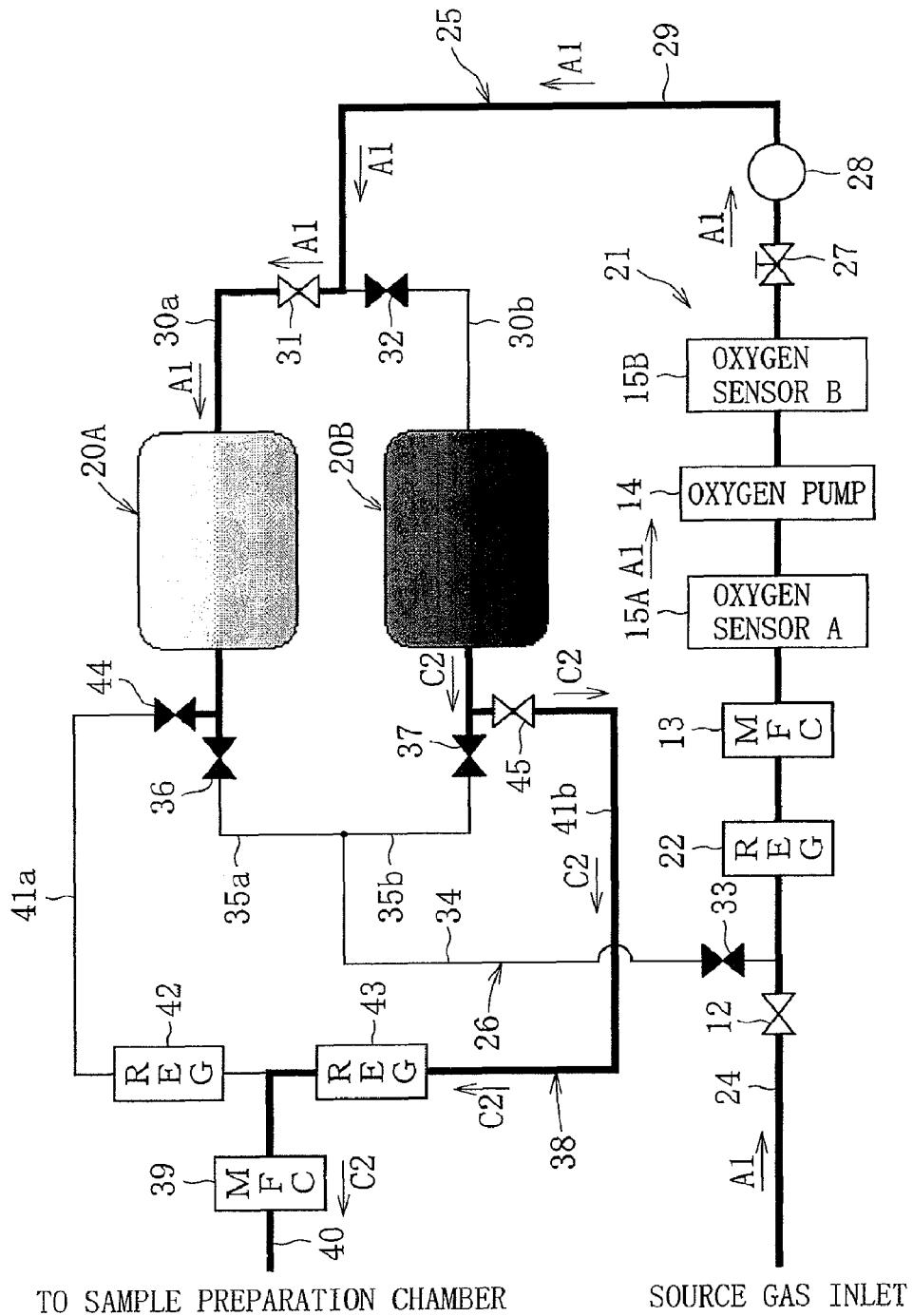
FIG. 5 A simplified schematic view of the oxygen partial pressure control unit representing a process of supplying the purified gas from the second tank to the sample preparation chamber and a process of filling the first tank with a gas.
Figure 6:
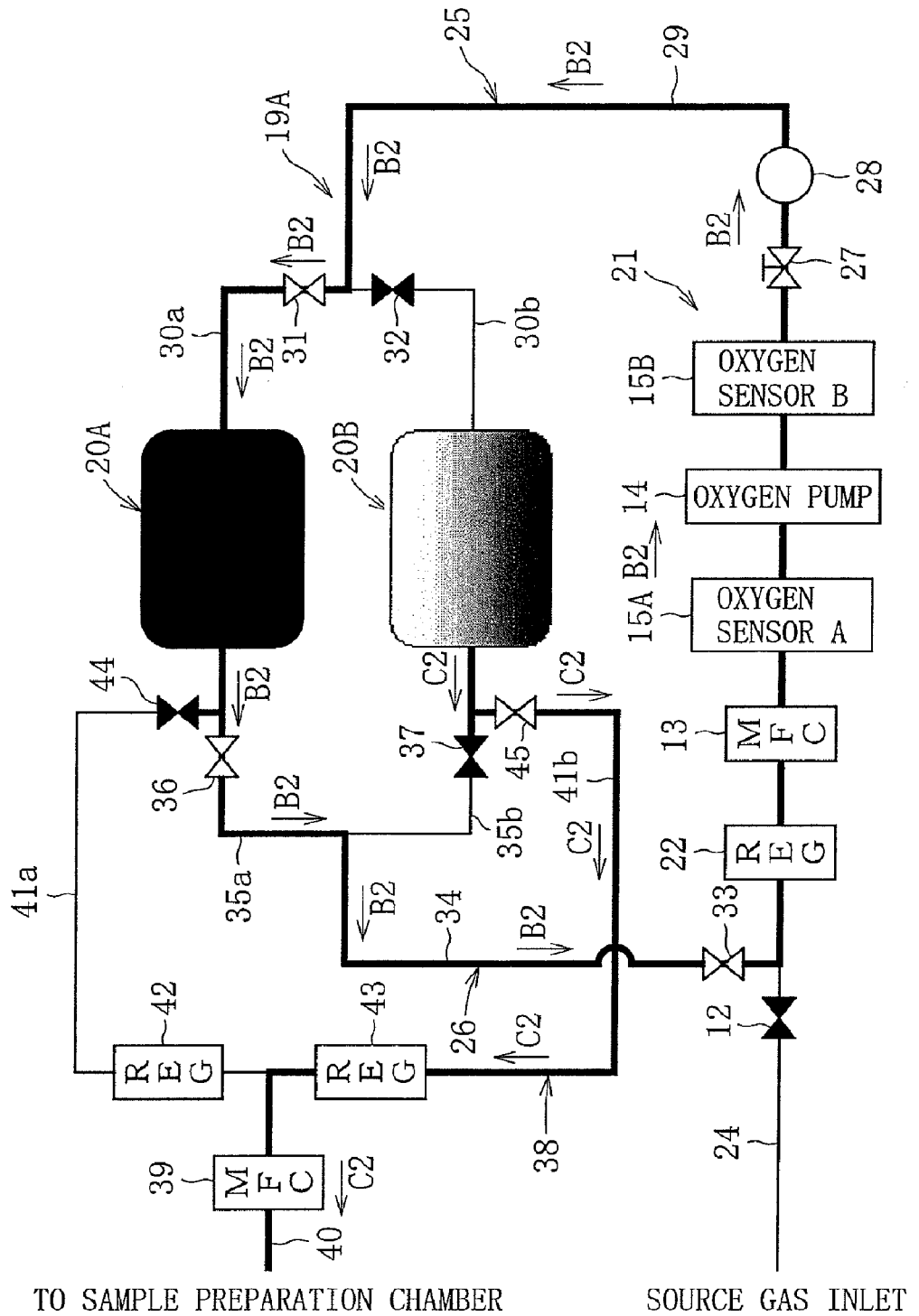
FIG. 6 A simplified schematic view of the oxygen partial pressure control unit representing the process of supplying the purified gas from the second tank to the sample preparation chamber and a process of purifying the gas of the first tank.
Figure 7:
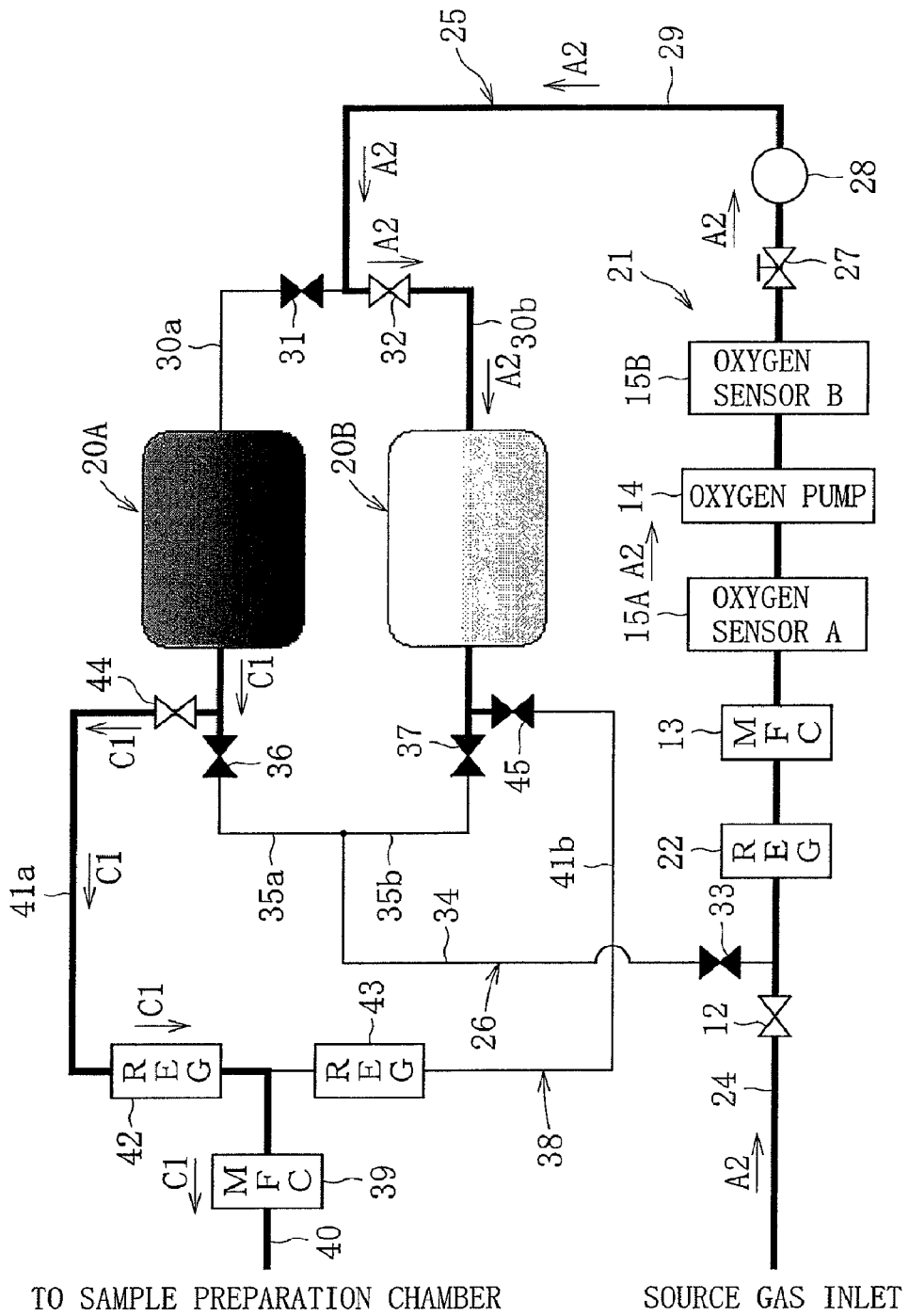
FIG. 7 A simplified schematic view of the oxygen partial pressure control unit representing the process of supplying the purified gas from the first tank to the sample preparation chamber and a process of filling the second tank with the source gas.

Next, a description is made of an operation of the oxygen partial pressure control unit illustrated in FIG. 1. In this case, there are provided: a process of filling each of the tanks 20A and 20B with a source gas as is illustrated in FIG. 2; a process of purifying the source gas of each of the tanks 20A and 20B with the oxygen partial pressure controlled within a range of from 0.2 to $10^{-30}$ atm as is illustrated in FIG. 3; a process of emitting (supplying) the purified gas of the first tank 20A to the sample preparation chamber or the like, and, at the same time, purifying the source gas of the second tank 20B into the purified gas as is illustrated in FIG. 4; a process of filling the first tank 20A with the source gas, and, at the same time, emitting (supplying) the purified gas of the second tank 20B to the sample preparation chamber or the like as is illustrated in FIG. 5; a process of purifying the gas of the first tank 20A, and, at the same time, emitting (supplying) the purified gas of the second tank 20B to the sample preparation chamber or the like as is illustrated in FIG. 6; and a process of emitting (supplying) the purified gas of the first tank 20A to the sample preparation chamber or the like, and, at the same time, filling the second tank 20B with the source gas as is illustrated in FIG. 7. It should be noted that, in FIGS. 2 to 7, the illustration of the oxygen partial pressure control section 17 and the like is omitted. Further, in FIGS. 2 to 7, with regard to the switching valves 12, 31, 32, 33, 36, 37, 44, and 45, a hollow mark indicates an open state, and a filled-in mark indicates a closed state. With regard to the circulation circuit 19, the gas outflow path 38, and a gas inflow path 24, a thick line indicates that the gas is flowing.

In the process illustrated in FIG. 2, with the switching valves 31 and 32 of the first circulation path 25 set to the open state, and the switching valves 33, 36, 37, 44, and 45 of the second circulation path 26 set to the closed state, the pump 28 is driven. With this, the source gas (process gas) passes through the switching valve 12 of the gas inflow path 24, and then flows into the first circulation path 25 via the gas purification section 21.

Then, the source gas flows into the main body pipe 29 of the first circulation path 25, and then, the flow rate thereof is regulated by the flow rate regulating valve 27. Then, the source gas flows into the branch paths 30a and 30b of the first circulation path 25 via the pump 28, and then flows into the tanks 20A and 20B from the branch paths 30a and 30b, respectively. The switching valves 36, 37, 44, and 45 of the second circulation path 26 are in the closed state, and hence the source gas that has flowed into the tanks 20A and 20B does not flow out to the second circulation path 26. Specifically, the source gas, which has not been processed yet, flows through the gas inflow path 24, the gas purification section 21 and the first circulation path 25 to the tanks 20A and 20B as indicated by arrows A, and is sequentially supplied to the tanks 20A and 20B, filling the tanks 20A and 20B.

In this manner, once the tanks 20A and 20B are filled with the source gas, the state illustrated in FIG. 2 is changed to a state illustrated in FIG. 3, in which the switching valve 12 is set to the closed state, and the switching valves 33, 36, and 37 of the second circulation path 26 are set to the open state.

With this, there is formed the circulation circuit 19 including the tanks 20A and 20B, the second circulation path 26, the gas purification section 21, and the first circulation path 25.

With the pump 28 driven, the gas circulates within the circulation circuit 19 as indicated by arrows B.

In this state, the gas purification section 21 purifies the gas flowing through the gas purification section 21. Specifically, the oxygen partial pressure setting section 16 sets the oxygen partial pressure to a desired value, for example, $1\times10^{-21}$ to $1\times10^{-30}$ atm. Then, a control signal for setting the oxygen partial pressure to the value set by the oxygen partial pressure setting section 16 is sent from the oxygen partial pressure control section 17 to the oxygen pump 14. The control signal controls a current I of the oxygen pump 14, and the oxygen partial pressure of the gas supplied to the oxygen pump 14 through the REG 22 and the mass flow controller (MFC) 13 is controlled to approximately $1\times10^{-21}$ to $1\times10^{-30}$ atm, which is set by the oxygen partial pressure setting section 16.

The gas flowing through the gas purification section 21 is monitored by the upstream oxygen sensor 15A and the downstream oxygen sensor 15B for the oxygen partial pressure thereof, and then, the monitor values thereof are displayed in the oxygen partial pressure display section 18 and also input to the oxygen partial pressure control section 17. In this manner, the monitor values monitored by the oxygen sensors 15A and 15B are input to the oxygen partial pressure control section 17, and then compared with the set value set by the oxygen partial pressure setting section 16. As a result, it is checked whether or not the oxygen partial pressure of the gas, which is controlled by the oxygen pump 14, is controlled to be the set value by the oxygen partial pressure setting section 16. Then, if the oxygen partial pressure monitored by the oxygen sensor 15B does not coincide with the oxygen partial pressure set by the oxygen partial pressure setting section 16, a control signal is output from the oxygen partial pressure control section 17 to the oxygen pump 14, and the current I flowing through the oxygen pump 14 is regulated, whereby a gas (purified gas) having the oxygen partial pressure controlled to approximately $1\times10^{-21}$ to $1\times10^{-30}$ atm is supplied to the first circulation path 25.

Due to this, the purified gas is supplied to the tanks 20A and 20B, and the gas (mixed gas of purified gas and unprocessed source gas) flows out of the tanks 20A and 20B to the second circulation path 26 by the amount corresponding to the amount of the gas that has flowed into the tanks 20A and 20B, causing that gas to flow through the gas purification section 21 again. With this, the oxygen partial pressure of the gas flowing into the gas purification section 21 is controlled to approximately $1\times10^{-21}$ to $1\times10^{-30}$ atm, and the resultant gas (purified gas) is supplied to the first circulation path 25. In other words, with the gas flowing within the circulation circuit 19, the gas purified to have the oxygen partial pressure controlled to approximately $1\times10^{-21}$ to $1\times10^{-30}$ atm is supplied to the tanks 20A and 20B.

In this manner, when the gas of the tanks 20A and 20B has been purified, the purified gas of each of the tanks 20A and 20B is sent to the sample preparation chamber. In this case, as illustrated in FIG. 4, the purified gas of the first tank 20A is first emitted to the sample preparation chamber. Specifically, from the state illustrated in FIG. 3, as illustrated in FIG. 4, the switching valve 31 of the first circulation path 25 is set to the closed state, and the switching valve 36 and switching valve 44 of the second circulation path 26 are set to the closed state and the open state, respectively.

With this, the purified gas of the first tank 20A at positive pressure flows out to the first connecting pipe 41a of the outflow path 38. Then, the purified gas is emitted to the sample preparation chamber via the mass flow controller (MFC) 39 that controls the flow rate of the purified gas coming through the pressure regulating valve (REG) 42 to a set value. Specifically, the purified gas of the first tank 20A flows along the outflow path 38 as indicated by arrows C1, and then is supplied to the sample preparation chamber.

Further, the gas within the tank 20B circulates, as indicated by arrows B1, along a circulation circuit 19B including the second tank 20B, the branch pipe 35b, the main body pipe 34, the gas purification section 21, the main body pipe 29, and the branch pipe 30b, with the result that the gas purification is continued.

When the supply of the purified gas of the first tank 20A to the sample preparation chamber is finished, as illustrated in FIG. 5, the purified gas of the second tank 20B at positive pressure is emitted to the sample preparation chamber. Specifically, from the state illustrated in FIG. 4, as illustrated in FIG. 5, the switching valve 31 of the first circulation path 25 is set to the open state, and the switching valve 32 thereof is set to the closed state. Further, the switching valves 33, 37, and 44 of the second circulation path 26 are set to the closed state, and the switching valve 45 thereof is set to the open state.

With this, the purified gas of the second tank 20B flows out to the first connecting pipe 41b of the outflow path 38. Then, the purified gas is emitted to the sample preparation chamber via the mass flow controller (MFC) 39 that controls the flow rate of the gas coming through the pressure regulating valve (REG) 43 to the set value. Specifically, the purified gas of the second tank 20B flows along the outflow path 38 as indicated by arrows C2, and then is supplied to the sample preparation chamber.

Further, in the state illustrated in FIG. 5, the source gas is supplied to the gas inflow path 24. Specifically, as indicated by arrows A1, the source gas flows through the gas inflow path 24, the gas purification section 21, and the main body pipe 29 and the branch pipe 30a of the first circulation path 25 to the first tank 20A to be supplied to the first tank 20A, whereby the first tank 20A is filled with the source gas.

Next, as illustrated in FIG. 6, the source gas filled in the first tank 20A is purified. Specifically, from the state illustrated in FIG. 5, as illustrated in FIG. 6, the switching valves 36 and 33 of the second circulation path 26 are set to the open state. With this, the gas circulates, as indicated by arrows B2, along a circulation circuit 19A including the first tank 20A, the branch pipe 35a and main body pipe 34 of the second circulation path 26, the gas purification section 21, and the main body pipe 29 and branch pipe 30a of the first circulation path 25.

Owing to this circulation, the gas of the first tank 20A is purified again. During the gas purification, the purified gas of the second tank 205 flows along the outflow path 38 as indicated by the arrows C2, and is supplied to the sample preparation chamber.

Further, when the supply of the purified gas of the second tank 20B to the sample preparation chamber is finished, as illustrated in FIG. 7, the second tank 20B is filled with the source gas again. Specifically, from the state illustrated in FIG. 6, as illustrated in FIG. 7, the switching valve 31 of the first circulation path 25 is set to the closed state, and the switching valve 32 thereof is set to the open state. Further, the switching valves 33, 36, and 45 of the second circulation path 26 are set to the closed state, and the switching valve 44 thereof is set to the open state.

With this, as indicated by arrows A2, the source gas flows through the gas inflow path 24, the gas purification section 21, and the main body pipe 29 and the branch pipe 30b of the first circulation path 25 to the second tank 20B to be supplied to the second tank 20B, whereby the second tank 20B is filled with the source gas.

Further, while the second tank 20B is being filled with the source gas, the purified gas flows out from the first tank 20A to the connecting pipe 41a of the gas outflow path 38. Specifically, the purified gas of the first tank 20A flows along the outflow path 38 as indicated by the arrows C1, and is supplied to the sample preparation chamber. Subsequently, the processing returns to the process illustrated in FIG. 4, and the above-mentioned processes are repeated until the unit stops operating.

In this manner, the purified gas having the oxygen partial pressure controlled to $2 \times 10^{-1}$ to $1 \times 10^{-30}$ atm is continuously supplied to the sample preparation chamber.

According to the present invention, the purified gas that has been produced by the gas purification section 21 can be stored in the tank 20, and hence it is possible to provide stable supply of the purified gas to another unit. Moreover, the purified gas is produced from the gas circulating within the circulation circuit 19, and hence it is possible to produce the purified gas in a clean state, enabling a purified gas of high quality to be supplied to another unit. In other words, with a unit in which the purified gas that has been supplied to another unit and used is returned and sequentially supplied to the gas purification section 21, it is difficult to maintain the clean state, and there is a fear of deteriorated quality. In addition, the purified gas can be stored in a plurality of the tanks 20, and hence it is possible to enhance the capacity to supply the purified gas to another unit.

Then, the switching valves 31 and 32 and the like form a first switching means 51 for switching between permission and suspension of the supply of the purified gas produced by the gas purification section 21 to the respective tanks, whereas the switching valves 36, 37, 44, and 45 and the like form a second switching means 52 for switching between the permission and the suspension of the supply of the purified gas stored within the respective tanks 20A and 20B to another unit.

Accordingly, switching of the first switching means 51 and the second switching means 52 (in this case, formed by the switching valves 31, 32, 36, 44, and the like) permits the supply of the purified gas from the first tank 20A to another unit (sample preparation chamber or the like), and switching of the first switching means 51 and the second switching means 52 (in this case, formed by the switching valves 31, 32, 33, 37, 45, and the like) enables the second tank 20B that has finished supplying the purified gas to another unit to be filled with the source gas, and enables the purification by the gas purification section 21, in a state in which the supply of the gas from the first tank 20A is permitted.

In other words, according to the present invention, the switching of the first switching means 51 and the second switching means 52 enables the gas purified through circulating within the unit to be continuously emitted to another unit. As a result, processing that uses the purified gas is stably performed by another unit. It should be noted that the first switching means 51 and the second switching means 52 can be respectively formed with combinations of switching valves arbitrarily selected from among the switching valves 31, 32, 33, 36, 37, 44, and 45 and the like.

The gas purification section 21 includes the electrochemical oxygen pump 14 capable of controlling the source gas to have the target oxygen partial pressure, and the oxygen sensor 15 that monitors the oxygen partial pressure of the gas. In other words, the gas having the oxygen partial pressure controlled to the target value can be purified by the oxygen pump 14, and also, the oxygen partial pressure of this purified gas can be checked, enabling the gas having the oxygen partial pressure controlled to the target value to be stably supplied to the tank. Further, the oxygen sensors 15A and 15B are disposed upstream and downstream of the oxygen pump 14, and hence it becomes easier to regulate the gas to be purified by the oxygen pump 14, with the result that a gas having the oxygen partial pressure controlled more accurately can be purified.

Figure 8:
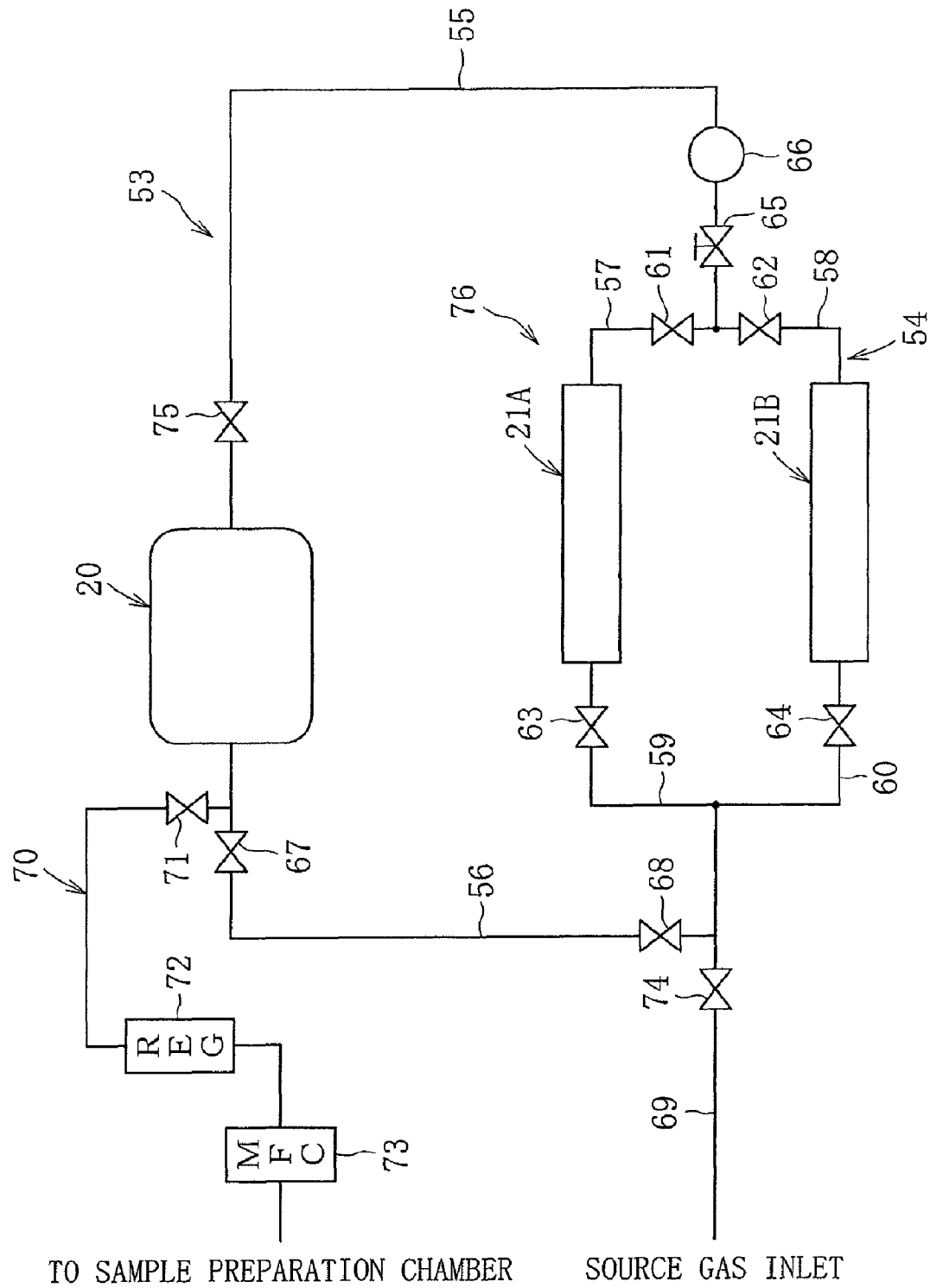
FIG. 8 A simplified schematic view of the oxygen partial pressure control unit representing another embodiment of the present invention.
Figure 9:
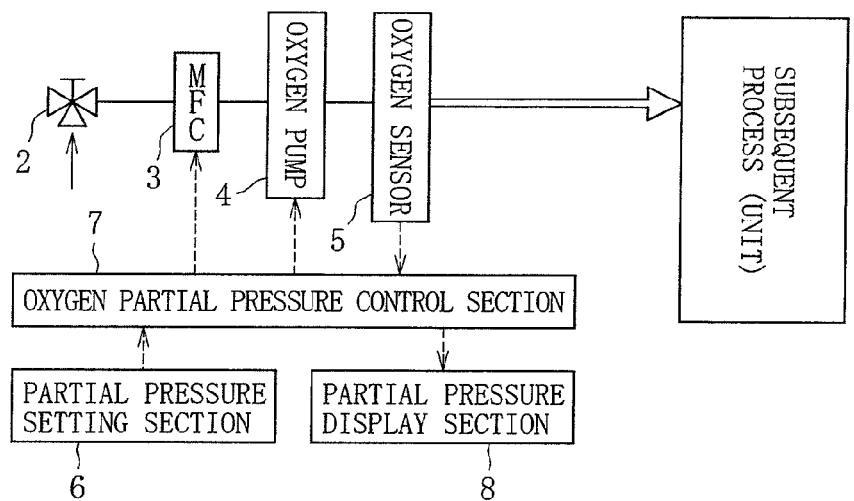
FIG. 9 A simplified schematic view of a conventional oxygen partial pressure control unit.

Next, FIG. 8 illustrates another embodiment, and, in this case, a plurality of (in the example of FIG. 8, two) gas purification sections 21A and 21B are provided. Each of the gas purification sections 21A and 21B has the same configuration as that of the gas purification section 21 illustrated in FIG. 1, and hence a description thereof is omitted. In this unit as well, a circulation circuit 53 including the tank (buffer tank) 20, the gas purification sections 21A and 21B, and the like is formed, and the purified gas stored in the tank 20 is supplied to the sample preparation chamber.

The circulation circuit 53 includes a purification circuit section 54 including the gas purification sections 21A and 21B, a first connecting pipe 55 connecting the downstream side of the purification circuit section 54 and the tank 20, and a second connecting pipe 56 connecting the upstream side of the purification circuit section 54 and the tank 20.

The purification circuit section 54 includes a pair of the gas purification sections 21A and 21B disposed in parallel with each other, junction pipes 57 and 58 that connect the downstream sides of the gas purification sections 21A and 21B, and branch pipes 59 and 60 that connect the upstream sides of the gas purification sections 21A and 21B. Switching valves 61, 62, 63, and 64 are interposed in the junction pipes 57 and 58 and the branch pipes 59 and 60, respectively.

In the first connecting pipe 55, a flow rate regulating valve 65, a pump (for example, diaphragm pump) 66, and a switching valve 75 are interposed. In the second connecting pipe 56, switching valves 67 and 68 are interposed. A gas inflow pipe 69 in which a switching valve 74 is interposed is connected to a junction portion of the branch pipes 59 and 60, and the second connecting pipe 56 is connected to the gas inflow pipe 69 on the downstream side of the switching valve 74.

A gas outflow pipe 70 is connected to the second connecting pipe 56. In the gas outflow pipe 70, a switching valve 71, an REG 72, and an MFC 73 are interposed. It should be noted that the gas outflow pipe 70 is connected to the second connecting pipe 56 on the upstream side of the switching valve 67.

Next, a description is made of an operation of the unit illustrated in FIG. 8. First, the source gas is stored in the tank 20. Specifically, the switching valves 61, 62, 63, and 64 of the purification circuit section 54 are set to the open state, and the switching valves 67 and 68 of the second connecting pipe 56 are set to the closed state. Further, the switching valve 71 of the gas outflow pipe 70 is set to the closed state.

With this, the source gas that has entered the gas inflow pipe 69 flows through the purification circuit section 54 and the first connecting pipe 55 to the tank 20, and the tank 20 is filled with the source gas. After that, the switching valve 74 of the gas inflow pipe 69 is set to the closed state, and the switching valves 67 and 68 of the second connecting pipe 56 are set to the open state. With this, the gas circulates along the circulation circuit 53 including the tank 20, the second connecting pipe 56, the purification circuit section 54, and the first connecting pipe 55. This circulation enables the purification circuit section 54 to purify the gas having the oxygen partial pressure controlled within a range of from 0.2 to $10^{-30}$ atm, and the gas filled in the tank 20 is purified.

In this manner, once the gas of the tank 20 is purified, this purified gas of the tank 20 can be supplied to the sample preparation chamber. Specifically, the switching valve 75 of the first connecting pipe 55 is set to the closed state, and the switching valves 67 and 68 of the second connecting pipe 56 are set to the closed state. Further, the switching valve 71 of the gas outflow pipe 70 is set to the open state. Accordingly, the purified gas of the tank 20 flows out to the gas outflow pipe 70, and the purified gas can be supplied to the sample preparation chamber via the REG 72 and the MFC 73.

Incidentally, because the purification circuit section 54 is provided with the pair of the gas purification sections 21A and 21B, the gas may only be purified by any one of them. Specifically, in a case where the gas is purified by the first gas purification section 21A and the second gas purification section 21B does not purify the gas, the switching valves 62 and 64 have only to be set to the closed state. Further, conversely, in a case where the gas is purified by the second gas purification section 21B and the first gas purification section 21A does not purify the gas, the switching valves 61 and 63 have only to be set to the closed state.

In the unit illustrated in FIG. 8, by using the switching valves 61, 62, 63, and 64, and the like, it is possible to form a third switching means 76 that switches between the permission and the suspension of the supply of the purified gas to the tank from each of the gas purification sections. With the switching of this third switching means 76, it is possible to cause the gas to circulate through any gas purification section among a plurality of the gas purification sections.

With the unit illustrated in FIG. 8, which is provided with the plurality of the gas purification sections 21, it is possible to increase the gas purification capacity, enabling stable supply of the purified gas to another unit. For this reason, it is also possible to satisfactorily handle a unit that requires a large amount of the purified gas, making applications for the gas supply free from limitation.

In addition, with the switching of the third switching means 76, the number of the gas purification sections through which the gas is to be caused to circulate can be changed, and hence the purification capacity for the gas can be changed. Thus, it is possible to perform an efficient operation by changing the purification capacity in accordance with the amount of gas use of another unit of a supply target.

Further, though illustration thereof is omitted, as another embodiment, a plurality of the tanks 20 and a plurality of the gas purification sections 21 may be provided. In this manner, by providing the plurality of the tanks 20 and the plurality of the gas purification sections 21, it is possible to attain the functional effect of the unit illustrated in FIG. 1 and the functional effect of the unit illustrated in FIG. 8, and therefore it becomes possible to perform a more accurate operation in accordance with the amount of gas use of another unit of the supply target. This enables a high-efficiency operation, and the another unit is stably supplied with the purified gas, resulting in creation of high quality samples and the like.

Hereinabove, the embodiments of the present invention have been described, but the present invention is not limited to the above-mentioned embodiments, and a variety of modifications can be made. For example, in the oxygen partial pressure control unit illustrated in FIG. 1 and other figures, the number of tanks may be one or three or more. In the case where three or more tanks are provided, the purified gas can be supplied to the sample preparation chamber or the like at the same time from two or more tanks, or the purified gas can be stored in two or more tanks. An operation can be selected from a variety of options in accordance with the amount of gas use or the like. Further, in the oxygen partial pressure control unit illustrated in FIG. 8, three or more gas purification sections may be provided.

Incidentally, in the above-mentioned embodiments, the oxygen sensors 15A and 15B are disposed upstream and downstream of the oxygen pump 14, but the upstream oxygen sensor 15A may be omitted. Specifically, the oxygen partial pressure of the gas purified by the oxygen pump 14 only needs to be checked and controlled to a desired value. Accordingly, the downstream oxygen sensor 15B alone can sufficiently control the partial pressure to a desired value.

Further, in a case where there is no need to consider the generation of impurities in the sample preparation chamber or in a case where generated impurities can be removed, the used purified gas discharged from the sample preparation chamber may be returned to the gas purification section 21 and recycled. If new supply gas is to be used for the whole of the inert gas to be supplied to the sample preparation chamber, in addition to the increased load on the oxygen pump 14 and the increased size and cost for the installation, the installation space becomes larger and the cost for controlling the oxygen partial pressure to a predetermined value becomes higher as well.

However, the used purified gas discharged from the sample preparation chamber is obviously higher in oxygen partial pressure compared to the purified gas that has been subjected to the oxygen partial pressure control in the oxygen pump 14 and is supplied to the sample preparation chamber, but much lower in oxygen partial pressure compared to a new supply gas that is supplied from a valve for inflow 2. Accordingly, if a return pipe or the like is provided and the used purified gas discharged from the sample preparation chamber is returned to the gas purification section 21 and recycled, compared to the case where only a new source gas is supplied, it is possible to not only reduce the amount of use of the supply gas but also reduce the load on the oxygen pump 14 and realize downsizing and low pricing. Further, it is also possible to reduce the installation space and the cost for controlling the oxygen partial pressure to the predetermined value.

INDUSTRIAL APPLICABILITY

The purified gas having the controlled oxygen partial pressure can be supplied to a die bonder, a solder proportioning ejection unit, or the like. The die bonder is a unit that bonds a die (silicon substrate chip on which electronic circuits are manufactured) to a lead frame, a base material, or the like by using solder, gold plating, or resin as a bonding material. Further, the solder proportioning ejection unit is a dispenser that ejects a liquid material (solder) used for bonding/connecting, for example, electrical parts, electronic parts, precision parts, and the like.

The invention claimed is:

1. An oxygen partial pressure control unit, comprising:
   a gas purification section for purifying a gas having an oxygen partial pressure controlled within a range of from 0.2 to $10^{-30}$ atm; and
   a tank for storing the purified gas produced by the gas purification section, the oxygen partial pressure control unit supplying the purified gas stored within the tank to another unit,
   wherein the oxygen partial pressure control unit further comprises a circulation circuit comprising the tank and the gas purification section, and a source gas supplied to the oxygen partial pressure control unit is caused to circulate along the circulation circuit, and the purified gas produced by the gas purification section is stored in the tank.

2. An oxygen partial pressure control unit according to claim 1, wherein:

the circulation circuit comprises:
- a plurality of the tanks;
- a first switching means for switching between permission and suspension of supply of the purified gas produced by the gas purification section to each of the plurality of the tanks; and
- a second switching means for switching between permission and suspension of supply of the purified gas of the each of the plurality of the tanks to the another unit; and the circulation circuit is configured to:
- switch the second switching means to permit the supply of the purified gas from at least one of the plurality of the tanks to the another unit; and
- switch the first switching means to permit the supply of the purified gas to the tank that has finished the supply of the purified gas to the another unit, with the supply of the purified gas from the at least one of the plurality of the tanks permitted.

3. An oxygen partial pressure control unit according to claim 1, wherein:
the circulation circuit comprises:
- a plurality of the gas purification sections; and
- a third switching means for switching between permission and suspension of supply of the purified gas from each of the plurality of the gas purification sections to the tank; and the circulation circuit switches the third switching means to permit the gas to circulate through a desired gas purification section among the plurality of the gas purification sections.

4. An oxygen partial pressure control unit according to claim 1, wherein:
the circulation circuit comprises:
- a plurality of the tanks;
- a plurality of the gas purification sections;
- a first switching means for switching between permission and suspension of supply of the purified gas produced by the gas purification sections to each of the plurality of the tanks;
- a second switching means for switching between permission and suspension of supply of the purified gas of the each of the plurality of the tanks to the another unit; and
- a third switching means for switching between permission and suspension of supply of the purified gas from each of the plurality of the gas purification sections to the plurality of the tanks; and the circulation circuit is configured to:
- switch the second switching means to permit the supply of the purified gas from at least one of the plurality of the tanks to the another unit;
- switch the first switching means to permit the supply of the purified gas to the tank that has finished the supply of the purified gas to the another unit, with the supply of the purified gas from the at least one of the plurality of the tanks permitted; and
- switch the third switching means to permit the gas to circulate through a desired gas purification section among the plurality of the gas purification sections.

5. An oxygen partial pressure control unit according to claim 1, wherein the gas purification section comprises:
- an electrochemical oxygen pump capable of controlling the gas to a target oxygen partial pressure; and
- an oxygen sensor for monitoring the oxygen partial pressure of the gas.

6. An oxygen partial pressure control unit according to claim 5, wherein the oxygen sensor is a plurality of oxygen sensors, at least one of the oxygen sensors being disposed upstream of the electrochemical oxygen pump and at least one other of the oxygen sensors being disposed downstream of the electrochemical oxygen pump.

7. An oxygen partial pressure control unit according to claim 2, wherein the gas purification section comprises:
- an electrochemical oxygen pump capable of controlling the gas to a target oxygen partial pressure; and
- an oxygen sensor for monitoring the oxygen partial pressure of the gas.

8. An oxygen partial pressure control unit according to claim 3, wherein each of the gas purification sections comprises:
- an electrochemical oxygen pump capable of controlling the gas to a target oxygen partial pressure; and
- an oxygen sensor for monitoring the oxygen partial pressure of the gas.

9. An oxygen partial pressure control unit according to claim 4, wherein each of the gas purification sections comprises:
- an electrochemical oxygen pump capable of controlling the gas to a target oxygen partial pressure; and
- an oxygen sensor for monitoring the oxygen partial pressure of the gas.

10. An oxygen partial pressure control unit according to claim 7, wherein the oxygen sensor is a plurality of oxygen sensors, at least one of the oxygen sensors being disposed upstream of the electrochemical oxygen pump and at least one other of the oxygen sensors being disposed downstream of the electrochemical oxygen pump.

11. An oxygen partial pressure control unit according to claim 8, wherein, for each of the gas purification sections, the oxygen sensor is a plurality of oxygen sensors, at least one of the oxygen sensors being disposed upstream of the electrochemical oxygen pump and at least one other of the oxygen sensors being disposed downstream of the electrochemical oxygen pump.

12. An oxygen partial pressure control unit according to claim 9, wherein, for each of the gas purification sections, the oxygen sensor is a plurality of oxygen sensors, at least one of the oxygen sensors being disposed upstream of the electrochemical oxygen pump and at least one other of the oxygen sensors being disposed downstream of the electrochemical oxygen pump.

13. A supply method of supplying, to another unit, a purified gas having an oxygen partial pressure controlled within a range of from 0.2 to $10^{-30}$ atm, the supply method comprising:
- supplying, after storing the purified gas in a plurality of tanks, the purified gas from at least one of the plurality of tanks to the another unit;
- supplying, after finishing the supplying the gas from the at least one of the plurality of tanks, the purified gas from another one of the plurality of tanks to the another unit; and
- storing the purified gas in a tank that has finished supplying the purified gas during at least one of the supplying of the purified gas.

* * * * *